(12) United States Patent
Lucas (10) Patent No.: US 6,182,511 B1
(45) Date of Patent: Feb. 6, 2001

(54) ACOUSTIC BOTTLE TESTER AND CONVEYOR THEREFOR

(75) Inventor: Philip J. Lucas, Lakewood, CO (US)

(73) Assignee: Coors Brewing Company, Golden, CO (US)

( * ) Notice: Under 35 U.S.C. 154(b), the term of this patent shall be extended for 0 days.

(21) Appl. No.: 09/349,271

(22) Filed: Jul. 7, 1999

Related U.S. Application Data (63) Continuation-in-part of application No. 09/060,391, filed on Apr. 14, 1998, now Pat. No. 6,035,718.

(51) Int. Cl.[7] .................................................. G01N 29/00
(52) U.S. Cl. ............................ 73/630; 73/492; 198/471.1
(58) Field of Search ........................... 73/49.2, 600, 630, 73/801, 818; 198/471.1, 689.1

(56) References Cited

U.S. PATENT DOCUMENTS

| | | | | |
|---|---|---|---|---|
| 4,252,232 | * | 2/1981 | Beck et al. | 198/443 |
| 4,560,060 | * | 12/1985 | Lenhart | 198/803.5 |
| 5,939,620 | * | 8/1999 | Strand | 73/49.2 |
| 5,960,933 | * | 10/1999 | Albrecht | 198/689.1 |
| 6,035,718 | * | 3/2000 | Lucas | 73/630 |

* cited by examiner

Primary Examiner—Max Noori
(74) Attorney, Agent, or Firm—Klaas, Law, O'Meara & Malkin, P.C.; William P. O'Meara; Joseph J. Kelly (57) ABSTRACT

A vacuum conveyor for transporting articles across a space wherein the conveyor belt for the vacuum conveyor has a plurality of equally spaced apart fluid passageways formed therein and wherein a one way valve is installed in each fluid passageway so that when one of the fluid passageways is exposed to a vacuum source to hold an object on the conveyor belt the object will be held on the conveyor belt until a sufficient force is applied to the object to separate the object from the conveyor belt.

20 Claims, 6 Drawing Sheets

ACOUSTIC BOTTLE TESTER AND CONVEYOR THEREFOR

This application is a continuation-in-part of U.S. patent application Ser. No. 09/060,391 filed Apr. 14, 1998 for Acoustic Bottle Tester, now U.S. Pat. No. 6,035,718.

FIELD OF THE INVENTION

BACKGROUND OF THE INVENTION

The present invention relates generally to method and apparatus for inspecting bottles and, more particularly, to a method and apparatus for inspecting bottles which employs sound waves which rupture flawed bottles but which leave unflawed bottles undamaged.

Figure 1:
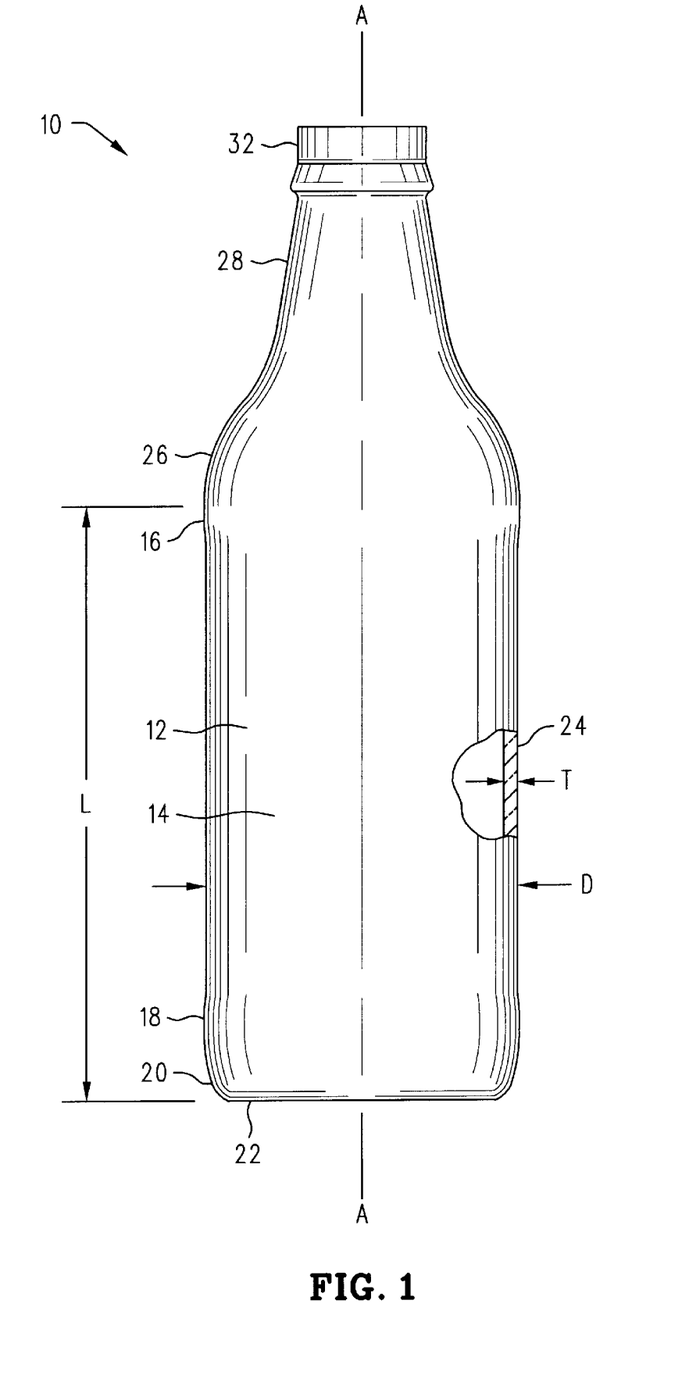
FIG. 1 is an elevation view of a bottle with a partially broken-away sidewall portion.
Figure 2:
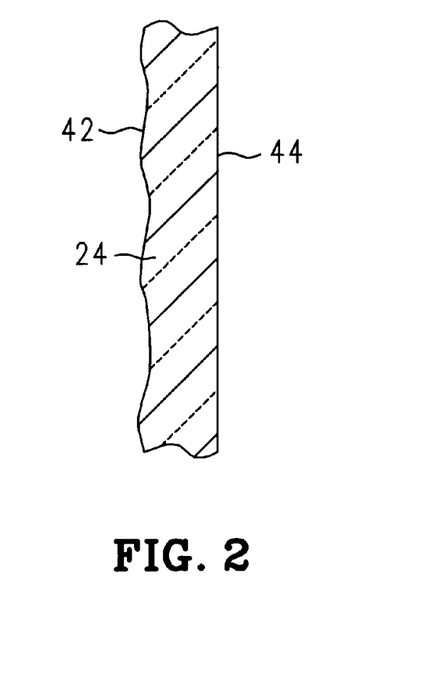
FIG. 2 is a cross-sectional elevation view of an unflawed portion of a bottle side wall.
Figure 3:
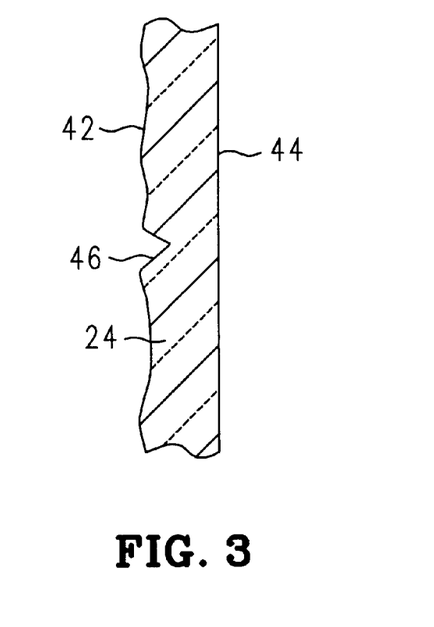
FIG. 3 is a cross-sectional elevation view of a portion of a bottle side wall having a fracture therein.

FIG. 1 shows a conventional "convenience" bottle having a side wall 24. The side wall 24, as illustrated in FIGS. 2 and 3, has an exterior surface 42 and an interior surface 44. The exterior surface 42 is typically somewhat rougher than the interior surface 44. The interior surface may be made smoother by a bottle-forming technique known as "firepolishing" which increases the strength of the bottle. FIG. 3 shows a fracture 46 in the exterior surface 42 of the bottle. A fracture 46 acts as a stress concentrater which significantly reduces the rupture strength of the bottle. The degree to which such a fracture 46 reduces the burst strength of the bottle varies with the depth of the fracture and the type of fracture. Table I illustrates data compiled by American Glass research showing the effect of different types of fractures on the breaking strength of soda lime glass bottles, the breaking load being indicated in pounds per square inch.

| Bottle Surface Condition of Bottle | Long Time Load | 20-min | ASTM 1-minute | 1-second | Impact <1 ms |
|---|---|---|---|---|---|
| Pristine-Inside of Bottle Fire Polished | 45000 | 63750 | 75000 | 100500 | 150000 |
| Pristine Molded | 12000 | 17000 | 20000 | 26800 | 40000 |
| Mild Abrasions | 6000 | 8500 | 10000 | 13500 | 20000 |
| Moderate Abrasion (produced by 320 Grit sand paper) | 2500 | 3400 | 4000 | 5400 | 8000 |
| Moderately Severe Abrasion (produced by 150 Grit sandpaper) | 2250 | 2850 | 3350 | 4500 | 5700 |
| Severe Abrasion (produced by Diamond Scratch) | 1700 | 2125 | 2500 | 3350 | 5000 |
| Deep Bruises in Glass | 650 | 1275 | 1500 | 2000 | 3000 |
| Cracks in Glass | 470 | 640 | 750 | 1000 | 1500 |

From the above table it may be seen that even very mild abrasions reduce the breaking strength of pristine-molded glass bottles (without inside fire polish) by 50% and that abrasions as small as 0.0005 inches in depth (150 grif sand paper) reduce the strength of pristine-molded glass bottles by 86%. It will also be appreciated that such small surface abrasions may be very difficult to detect by visual inspection. In addition to surface abrasions, there are a number of other types of flaws which reduce the breaking strength of a glass bottle including: score fractures, impact fractures, glass impurity fractures, stress concentrators due to improper melt temperature or improper cooling and stress concentrators caused by non-homogeneous compositions of glass and due to non-uniform glass distribution in the mold.

It is desirable for quality control purposes to test glass bottles after manufacture to determine whether flawed bottles are being created in the manufacturing process. The method for testing bottles most widely used in the industry today is known as a "squeeze tester". U.S. Pat. No. 5,351,552 of Giometti, which is hereby incorporated by reference, discloses such a squeeze tester. Bottles to be tested are moved along a conveyor belt which supports each bottle at its base. The bottles move along a path extending between a static wall on one side and the wall of a large rotating wheel on the other side. A bottle moving along the path is squeezed between the static wall and the moving wall provided by the large wheel, rotating as it moves along this portion of the path. The large wheel is biased towards the static wall and applies a predetermined pressure to the side wall of a bottle as it rotates through this portion of the bottle path. The bottle squeezer thus applies a selected amount of pressure in a direction perpendicular to the side wall of the bottle. The amount of pressure applied is selected to be less than that required to break an unflawed bottle, but more than that required to break a flawed bottle. ("Flawed bottle" as used herein is a relative term, the severity of bottle fracture to be detected being decided by quality control personnel who set the loading of the bottle tester to a value slightly higher than the strength of a bottle having such a fracture.) A problem with bottle squeezers has been that shattering glass from a flawed bottle may become imbedded in the side wall of the rotating wheel of the squeezer. This embedded glass or "stone" may cause scoring of bottles passing through the squeezer resulting in the flawing of bottles which were originally undamaged. If the flaw is generated towards the end of the rotation of the bottle through the squeezer, it may not be exposed to the maximum pressure of the squeezer and thus may pass through the squeezer unruptured, even though it is now flawed and has reduced rupture strength. Also, due to the fact that the wheel of the squeezer has a very large circumference compared to the circumference of a bottle, many bottles may pass through the squeezer which do not come into contact with the glass fragment imbedded in the squeezer wheel. Thus, it may be difficult to detect whether an increase in the number of flawed bottles detected by the squeezer has been caused by glass embedded in the squeezer wheel or other outside causes such as defects in the mold, etc. Another problem with bottle squeezers is that they cannot be operated at more than about 300 bottles per minute.

The following patents also relate to bottle squeezers and are hereby specifically incorporated by reference for all that is disclosed therein: U.S. Pat. No. 3,702,563 issued Nov. 14, 1972 of Brady et al; U.S. Pat. No. 3,729,082 issued Apr. 24, 1973 of Federko; U.S. Pat. No. 3,765,231 issued Oct. 16, 1973 of Erb et al; U.S. Pat. No. 3,777,556 issued Dec. 11, 1973 of Zappia; U.S. Pat. No. 4,021,122 issued May 3, 1977; U.S. Pat. No. 4,077,254 issued Oct. 4, 1994 of Mercer, Jr. et al; U.S. Pat. No. 4,096,939 issued Jun. 27, 1978 of Riggs et al; and U.S. Pat. No. 4,479,582 issued Oct. 30, 1984 of Ducloux.

OBJECTS OF THE INVENTION

It is an object of the invention to provide a bottle testing method and apparatus which obviates problems experienced with bottle squeezer testers.

It is another object of the invention to provide a method and apparatus for testing bottles which enables rapid on-line testing of bottles.

It is another object of the invention to provide a method and apparatus for testing bottles which does not require contact with the bottle sidewall.

It is another object of the invention to provide a method and apparatus for testing bottles which does not cause bottle degradation.

It is another object of the invention to provide a method and apparatus for testing bottles which is quickly and easily adjusted to test different bottle configurations.

It is another object of the invention to provide a method and apparatus for testing bottles which is relatively inexpensive to implement.

SUMMARY OF THE INVENTION

The present invention is directed to a method and apparatus for testing bottles which overcomes the above-described problems of prior art testers. In one preferred embodiment, the invention may comprise a bottle testing apparatus for testing bottles for flaws of a predetermined magnitude, said bottles having a predetermined bottle configuration and having at least one natural frequency (also sometimes referred to as resonant frequency) comprising a sound system which produces sound of a character sufficient to rupture one of said bottles having a flaw of at least said predetermined magnitude but insufficient to rupture one of said bottles not having a flaw of at least said predetermined magnitude.

The invention may also comprise a bottle tester comprising a) at least one wave form generator tuned to at least one operating frequency which is about equal to a natural frequency of a bottle to be tested; b) at least one amplifier in electrical communication with said at least one wave form generator; and c) at least one acoustic transponder in electrical communication with said audio amplifier and directed at said bottle to be tested.

The invention may also comprise a bottle tester for detecting flawed bottles comprising a) a first wave form generator generating a first wave form signal corresponding to a first natural frequency of a bottle to be tested; b) a second wave form generator generating a second wave form output signal corresponding to a second natural frequency of said bottle to be tested which is different from said first natural frequency; c) a signal mixer operably attached to receive said first and second wave form signals from said first and second wave form generators; d) a signal amplifier operably connected to said signal mixer; e) a first acoustic transponder having a first acoustic axis and having a signal input port operably connected to said signal amplifier; and f) a second acoustic transponder having a second acoustic axis positioned in coaxial alignment with said first acoustic axis and having a signal input port operably connected to said signal amplifier.

The invention may also comprise a method of determining whether bottles to be inspected are flawed comprising a) generating sound waves of a predetermined amplitude and having a frequency component which is a natural frequency of each bottle to be tested; and b) vibrating each bottle to be inspected with the sound waves.

In a preferred embodiment of the invention, a vacuum conveyor for use in performing the tests of this invention comprises a housing connected to a vacuum forming source to form a vacuum in the housing and the housing has at least one aperture formed therein. A conveyor belt is mounted for movement around portions of the housing. The conveyor belt has a plurality of equally spaced apart fluid passageways formed therein and is mounted so that the plurality of equally spaced apart fluid passageways pass over the at least one aperture so that a hollow object having an opening formed therein and in contact with the conveyor belt and surrounding at least one of the plurality of equally spaced apart fluid passageways will be held in contact with the conveyor belt by a vacuum force. Apparatus is provided for maintaining the vacuum force on the hollow object until a sufficient force is applied to separate the hollow object from the conveyor belt. The at least one aperture comprises a slot having a length extending in a direction parallel to the direction of movement of said conveyor belt and a transverse width wherein the length is greater than the width. Preferably, the length has an extent less than the distance between adjacent ones of the plurality of equally spaced apart fluid passageways. Successive ones of the plurality of equally spaced apart fluid passageways are spaced apart a distance so that the total cross-sectional area of at least one of the equally spaced apart fluid passageways is within the inner diameter of the opening of the hollow object. In a preferred embodiment, the apparatus comprises a one way valve associated with each one of the plurality of equally spaced apart fluid passageways and is located in each one of the plurality of equally spaced apart fluid passageways.

The housing has a length that is greater than its width and has a first end portion, a central portion, a second end portion, an upper surface and a lower surface. A vacuum chamber is located in the first end portion and is connected to the vacuum forming source. The at least one aperture is formed in the vacuum chamber. A first roll is mounted for rotation at the beginning of the first end portion and a second roll is mounted for rotation at the ending of the second end portion. The conveyor belt moves around the first and second rolls. A first guide apparatus is provided for guiding the movement of the conveyor belt over the upper surface and a second guide apparatus is provided for guiding the movement of the conveyor belt over the lower surface. The second guide apparatus applies a force on the conveyor belt to hold a portion of said conveyor belt in contact with said lower surface surrounding the at least one aperture so that the opening of the hollow object, which is in contact with said conveyor belt, is subjected to the vacuum force as it passes under the at least one aperture. The conveyor belt has opposite side edge portions and a central body portion with the opposite side edge portions being located between the lower surface and the second guide apparatus. In a preferred embodiment of the invention, the hollow object comprises a bottle having a neck portion having an opening formed therein so that the portion of the neck portion surrounding the opening contacts the central body portion. A bottle testing apparatus is provided and is located adjacent to the central portion so that the bottle is exposed to the bottle testing apparatus. The bottle testing apparatus breaks flawed bottles so that the vacuum holding force is removed and all of the broken bottle falls away from the conveyor belt.

BRIEF DESCRIPTION OF THE DRAWING

Illustrative and presently preferred embodiments of the invention are shown in the accompanying drawing in which.

DETAILED DESCRIPTION OF THE INVENTION

Figure 4:
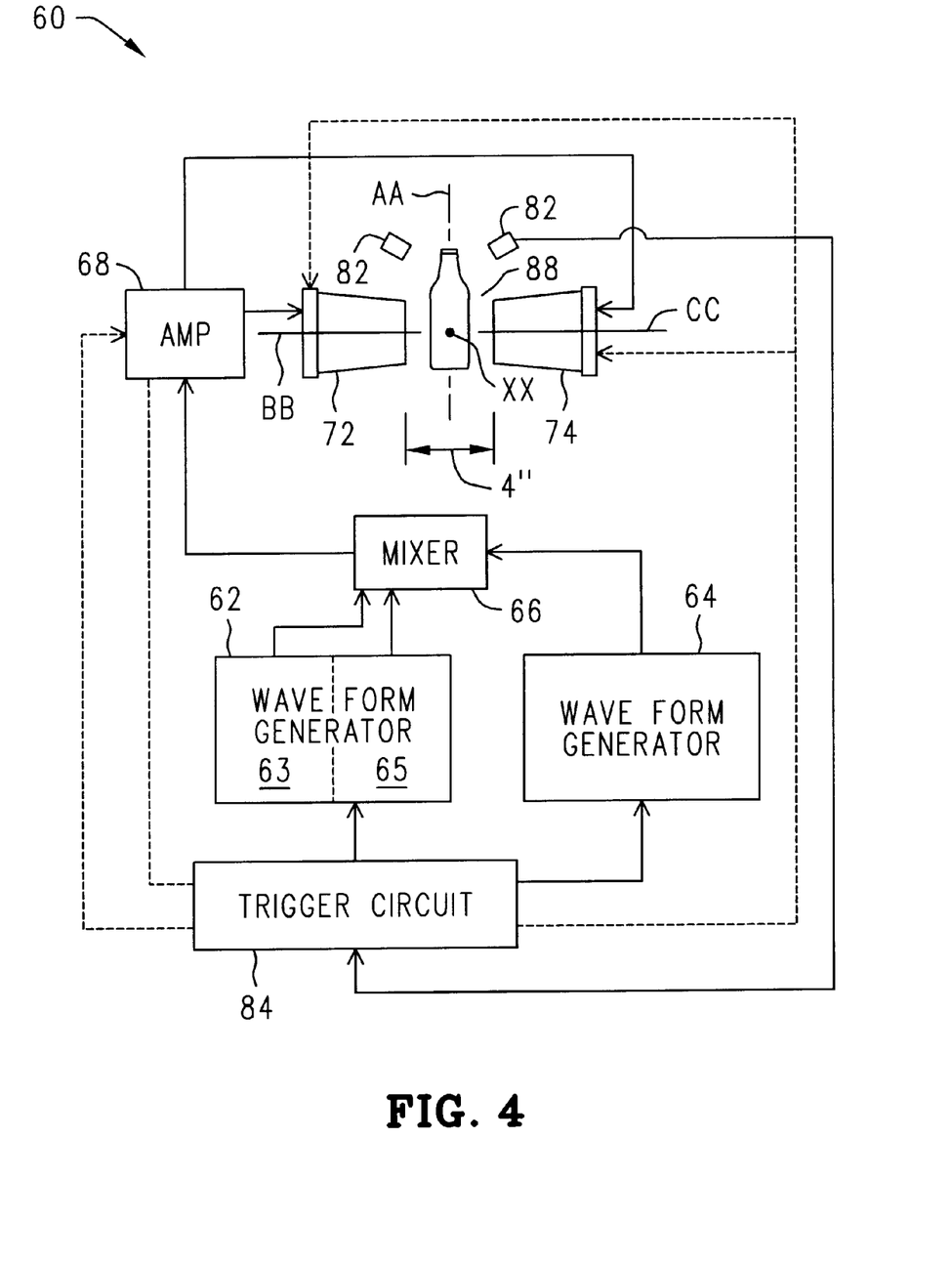
FIG. 4 is a schematic illustration of a bottle testing apparatus.
Figure 5:
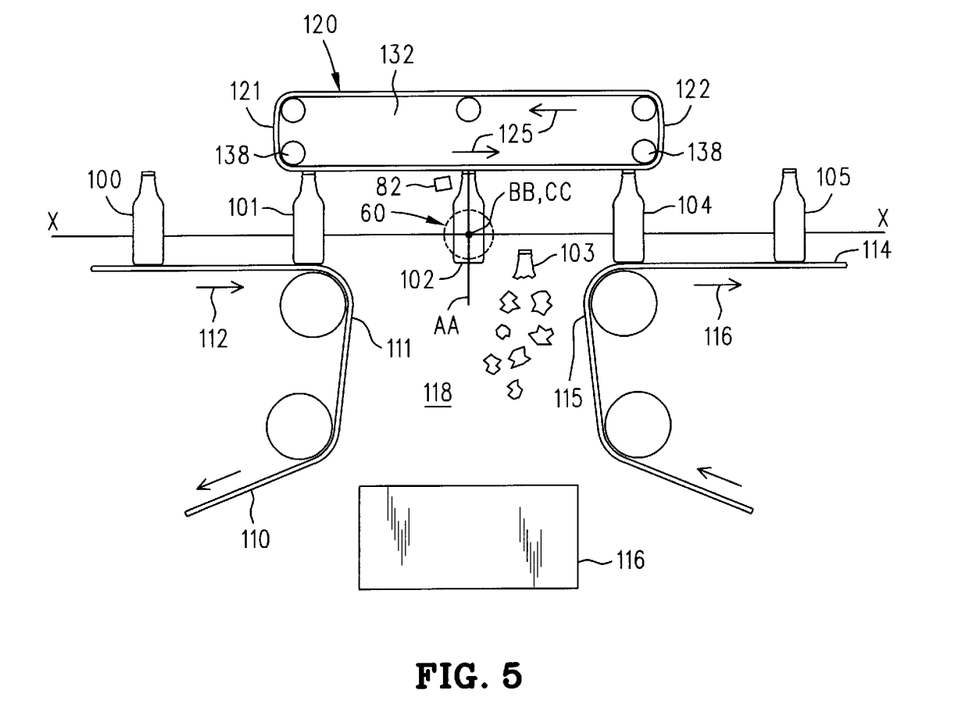
FIG. 5 is a schematic illustration of a conveyor assembly associated with a bottle testing apparatus.
Figure 6:
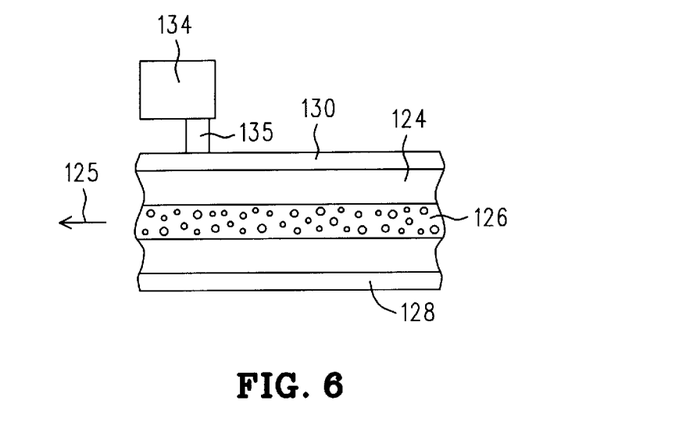
FIG. 6 is a schematic, bottom view of a portion of a vacuum conveyor belt assembly.
Figure 7:
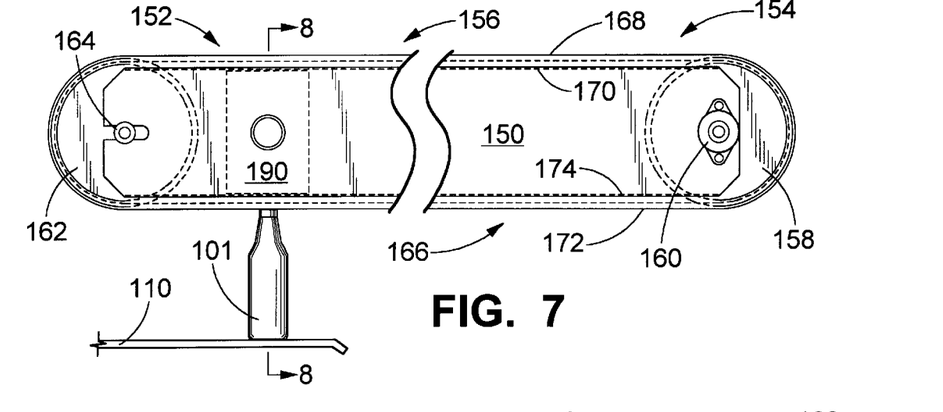
FIG. 7 is a schematic illustration of another preferred embodiment of the invention.

FIGS. 4 and 5, in general, show a bottle testing apparatus 60 for testing bottles 100–105 for flaws 46 of a predetermined magnitude, said bottles having a predetermined bottle configuration and having at least one natural frequency comprising a sound system 62, 64, 66, 68, 72, 74 which produces sound of a character sufficient to rupture one of said bottles having a flaw of at least said predetermined magnitude but insufficient to rupture one of said bottles not having a flaw of at least said predetermined magnitude.

FIG. 1 illustrates a conventional "convenience" bottle 10 having a central longitudinal axis AA. The bottle has a generally cylindrical body 12 with an intermediate portion 14, an upper bearing surface portion 16, a lower bearing surface portion 18 and a heel portion 20 which terminates at the bottle base 22. The body 12 has an annular wall 24 having a thickness "t" at the intermediate portion 14 of the body 12. The body 12 is integrally connected to an annular bottle shoulder 26 which is, in turn, integrally connected to a tapering bottle neck 28. The neck is integrally connected to an annular crown 32 which is adapted to receive a bottle cap (not shown). In one exemplary embodiment, bottle 10 has a body intermediate portion 14 having a diameter "D" of 2.5 inches and a wall thickness "t" of 0.060 inches. The length of the bottle body portion 12 is 4.5 inches. The upper and lower bearing surface portions 16, 18 may have a slightly thicker wall thickness, e.g. 0.08 inches and may each have a diameter of 2.6 inches. The shoulder 26 has a radius of curvature of 0.75 inches. The diameter of the bottle at the transition between the shoulder 26 and neck 28 is 1.25 inches. The radius of curvature of the bottle neck at its point of maximum curvature is 2.0 inches. The diameter of the bottle neck at the point of its connection to the crown is 1.0 inches. The diameter of the crown at its mid-portion is 0.88 inches. The diameter of the crown at the top of the bottle is 0.94 inches. The axial length of the shoulder is 1.5 inches. The axial length of the neck is 0.75 inches. The axial length of the crown is 0.25 inches. The diameter of the base is 2.5 inches.

As illustrated in FIGS. 2 and 3, the bottle side wall 24 has an exterior surface 42 and an interior surface 44. The exterior surface 42 is typically somewhat rougher than the interior surface 44. FIG. 3 illustrates a fracture 46 in the exterior surface of the bottle. Such fractures, as explained above, significantly reduce the strength of a bottle, causing it to rupture at much lower pressures than an unflawed bottle.

FIG. 4 schematically illustrates an acoustic bottle tester 60 which is used to test a bottle for fractures by applying sound waves to the bottle. The bottle tester may comprise one or more waveform generator units 62, 64. A waveform generator unit is an electronic device which is used to produce an electrical signal which is ultimately used to actuate an acoustic transponder to produce sound waves of a predetermined frequency. The waveform generator unit used may be any waveform generator units which can be used in association with an acoustic transponder to produce sound waves of desired frequency. A typical waveform generator has multiple channels and can produce a different frequency signal in each channel. As used herein "waveform generator" refers to the channel in a waveform generator unit which produces a single frequency wave. Thus, waveform generator 62 may have e.g., two channels 63, 65, each producing a different frequency signal. One conventional waveform generator unit which may be used for this purpose is Model No. 29 sold by Wavetek Company of San Jose, Calif. Other waveform generator units which might be used are commercially available from Hewlett-Packard Company of Palo Alto, Calif. and Tektronics, Inc., P.O. Box 1000, Wilsonville, Oreg. The waveform generators have outputs in electrical communication with a mixer 66. Mixers are conventional electronic devices which mix multiple waveform signals in order to provide a combined signal having a mixture of frequencies input to the mixer. A commercially available mixer which may be used for this purpose is Model No. CL-2, manufactured by Ashly Audio Inc. of 847 Holt Road, Webster, N.Y.. Other suitable mixers are available from JVC America of 41 Slater Drive, Elmwood Park, N.J. The signal output of the mixer is provided to an amplifier which may be any high-powered, acoustic amplifier. Commercially available acoustic amplifiers which may be used for this purpose include Model No. MFA-8000 available from Ashly Audio Inc. and comparable amplifiers available from JVC America. The mixed, amplified signal output by the amplifier is split into two channels, one channel being provided to drive first acoustic transponder (driver) 72 and the second channel being provided to drive second acoustic transponder 74. Acoustic transponders are well known acoustic devices which respond to an electronic input signal to produce sound waves of a frequency corresponding to the input signal. In one exemplary embodiment, the acoustic transponders are 8 ohm, 200 watt units which operate in a frequency range between 1500 hertz and 20 kilohertz. One commercially available transponder which may be used for this purpose is Model No. 2445-J manufactured by JVC America. The acoustic transponders 72, 74 have acoustic axes BB, CC, respectively, which are preferably positioned in coaxial alignment with the terminal ends of the transponders 72, 74 positioned approximately 4 inches apart. It is to be understood that the transducer assembly could include more or less than two transducers. At least two transducers are preferable since such a plural transducer assembly enables sound waves to be applied generally uniformly to the entire periphery of the bottle body. A larger transducer arrangement, such as for example, four transducers having two coaxially aligned pairs of transducers, rather than one pair, could be provided in order to increase the uniformity of pressure applied about the periphery of the bottle by the transducer sound waves. There is no limit to the number of the transducers which could be used except for physical space limitations associated with transducer placement around the bottle testing station. A bottle to be tested is positioned between the two transponders and receives an optimum amount of energy therefrom when the central longitudinal axis AA of the bottle is positioned in intersecting relationship with the axes BB, CC of the transponders. The bottle is preferably located at a height relative to the axes of the transponders such that axes BB, CC are positioned approximately midway along the length of the bottle body 12. A bottle sensor 82 is positioned near the acoustic transponders to detect when a bottle 10 is positioned at a bottle testing station 88 in alignment with the acoustic transponders. In one preferred embodiment, the bottle testing station comprises a region beginning 1.0 inches upstream of a point where bottle axis AA intersects transponder axes BB and CC to a point 1.0 inches downstream from this point of axes intersection. The bottle sensor 82 may comprise any sensor assembly capable of detecting the presence of a bottle such as, for instance, a photoelectric laser device which generates an electrical trigger signal whenever a laser beam positioned in a bottle path XX is interrupted by the passage of a bottle. As previously stated, any sensor device capable of detecting the presence of a bottle in the testing station and generating a signal in response thereto may be used. The trigger signal may be applied to any device which is in electrical communication with the waveform generators in order to actuate the sound system to produce sound waves that have impinged on a bottle to be tested. A device is in electrical communication with the waveform generator when it receives and/or processes the signal which is ultimately input to the sonic drivers 72, 74. Thus, the trigger signal could be used to actuate the drivers, or the amplifier, or the mixer or the waveform generators. In a preferred embodiment, it is used to actuate the signal generator.

FIG. 5 is a schematic illustration showing the online use of an acoustic bottle tester 60. In this embodiment, bottles are transferred in single-file relationship along a path XX toward the tester 60 by a first conveyor which may comprise a conventional belt conveyor 110 having a terminal end 111 located a short distance upstream of the bottle testing station 88. This conveyor moves bottles in belt direction 112. A second conveyor which may comprise a second conveyor belt 114 which moves bottles along path XX away from the tester in belt direction 116 has a terminal end 115 positioned a short distance downstream of testing station 88. The second conveyor belt has a terminal end 115 which may be positioned, e.g. four feet, from the terminal end 111 of the first belt conveyor. A vacuum conveyor 120 has a first end 121 positioned over a portion of the first conveyor belt 110 and has a second end 122 positioned over a portion of second conveyor belt 114. As illustrated in FIG. 5, the vacuum conveyor belt has a perforated central band portion 126 extending longitudinally down the middle thereof. The perforated band may have holes which may be, e.g., 1/16 in. in diameter having a density of, e.g., 64 holes per square inch. Sealing plates 128,130 are provided at the lateral sides of the vacuum conveyor in sealing, yet displaceable relationship with the edges of vacuum conveyor belt 124. The sealing plates and vacuum conveyor belt define a vacuum chamber 132 (shown in FIG. 5 with plate 128 removed). A vacuum pump 134 is in fluid communication with the vacuum chamber 132 through a conduit 135 extending through plate 130. The vacuum pump is of sufficient capacity to place the vacuum chamber 132 under sufficient negative pressure to suspend a bottle from the conveyor belt, i.e., a bottle is positioned with its finish end opening in engagement with perforated band 126 and the negative pressure in the vacuum chamber 132 is sufficiently high to resist the weight of the bottle and any inertial forces associated with conveying the bottle. The conveyor belt 124 rotates in belt direction 125. Conveyor belt rollers 136 and 138 located at the lower upstream and lower downstream end portions of the conveyor belt, respectively, temporarily block the application of suction through perforated band 126 at the portions which are momentarily engaged by these rollers. The removal of the vacuum force on the bottles as they pass beneath these rollers enables a smooth transition of each bottle from the first conveyor belt 110 onto the vacuum conveyor 120 and subsequently from the vacuum conveyor to the second conveyor belt 114.

The above-described conveyor assembly enables bottles 100,101, 102, 103, 104, 105 in a conveyor line to successively pass through testing station 88 without bottom support such that when a bottle is ruptured, the suction applied to the bottle is released and the ruptured bottle free falls into a trash bin 116 or the like. Thus, this assembly prevents broken glass from collecting on a bottle base support conveyor belt. The vacuum conveyor belt, since it covers the bottle opening, also prevents broken glass from a ruptured bottle from entering the opening of an adjacent bottle. The distance between conveyor belts 110 and 114 and the length of vacuum conveyor 120 may be adjusted as needed to prevent conveyor belts 110 and 114 and bottles supported thereon from being exposed to flying glass. Although one exemplary system for positioning bottles at the test station 88 has been specifically described herein, it is to be appreciated that the invention is not limited to this bottle positioning assembly. For example, the overhead vacuum conveyor could be replaced by any overhead conveyor system, such as a conventional type which engages a bottle neck or crown portion in order to suspend the bottle while it is being conveyed. One commercially available suspension-type conveyor system is sold under the product designation Ware Transfer by American Glass Research having business offices in Butler, Pa. It should also be appreciated that although a suspension type conveyor system in the bottle testing station region is preferable, a conventional base support conveyor belt could also be used in which glass debris from ruptured bottles could be removed from the conveyor system manually or by other means such as a vacuum or pressurized air. Also, the bottle tester 60 could be used off-line without a conveyor system. An off-line tester could support a bottle in front of the tester on a base support or through use of a neck clamp or neck ring support or any other support device which enables the body of the bottle to be exposed to sound waves from the transducers.

Figure 8:
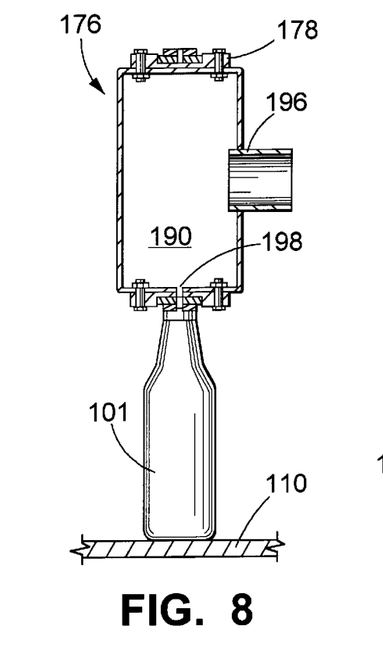
FIG. 8 is a cross-sectional view taken on the line 8—8 of FIG. 7.

Another preferred embodiment of a vacuum conveyor which can be used in this invention is illustrated in FIGS. 7–12. A housing 150 is mounted by suitable apparatus (not shown) at a fixed location and has a first end portion 152 and a second end portion 154 with a central body portion 156. A first roll 158 is mounted for rotation in suitable bearings 160 mounted on the second end portion 154. A second roll 162 is adjustably mounted on the first end portion 152 by suitable apparatus such as the slot arrangement 164. The second roll 162 preferably is an idler roll. A conveyor belt 166 is journalled for movement around the first and second rolls 158 and 162. The conveyor belt 166 has a upper portion or reach 168 that is moved over the upper surface 170 of the housing 150 and a lower portion or reach 172 that is moved over the lower surface 174 of the housing 150. The adjustable second roll 162 provides for the proper tensioning of the conveyor belt 166. A first guide apparatus 176, FIG. 8, is provided for guiding the movement of the conveyor belt 166 over the upper surface 170 and comprises a U-shaped member 178 secured to the upper surface 170 of the housing 150. The U-shaped member 178 is preferably formed from a plastic material having a relatively low coefficient of friction.

Figure 11:
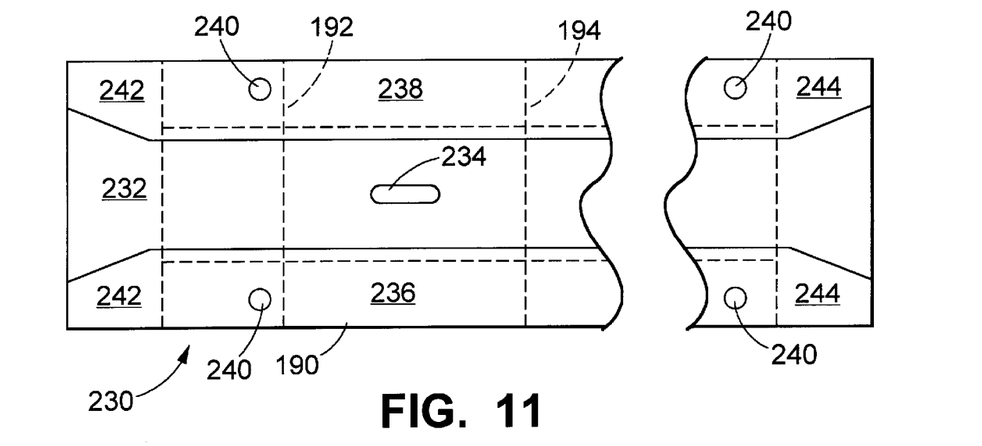
FIG. 11 is a partial bottom plan view of a portion of a preferred embodiment of the invention.

A vacuum chamber 190 is formed in the housing 150 by two spaced apart walls 192 and 194 secured to adjacent portions of the housing 150. A vacuum port 196 provides fluid communication between a vacuum creating source (not shown) and the vacuum chamber 190 to form a vacuum in the vacuum chamber. An aperture 198 is formed in the vacuum chamber 190. A preferred embodiment of the aperture 198 is illustrated in FIG. 11 and comprises a slot 200, FIG. 9, having a length extending in the direction of movement of the conveyor belt 166 that is greater than its width and is further discussed below.

Figure 9:
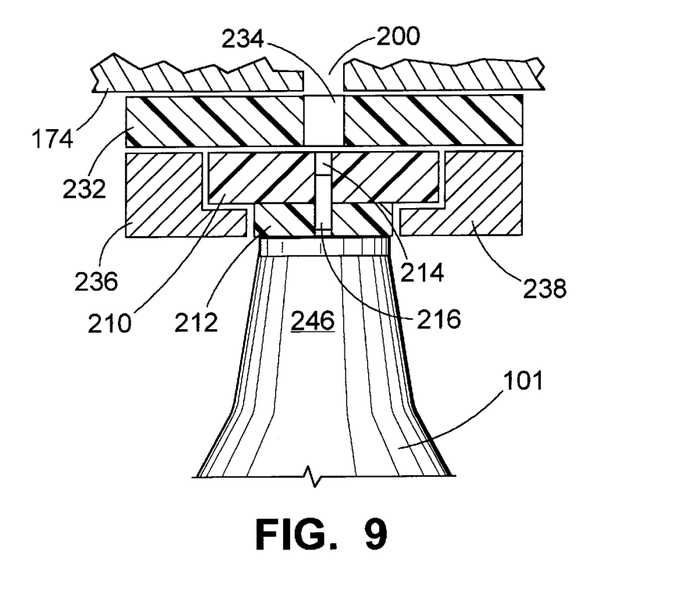
FIG. 9 is an enlargement of a portion of FIG. 8.
Figure 12:
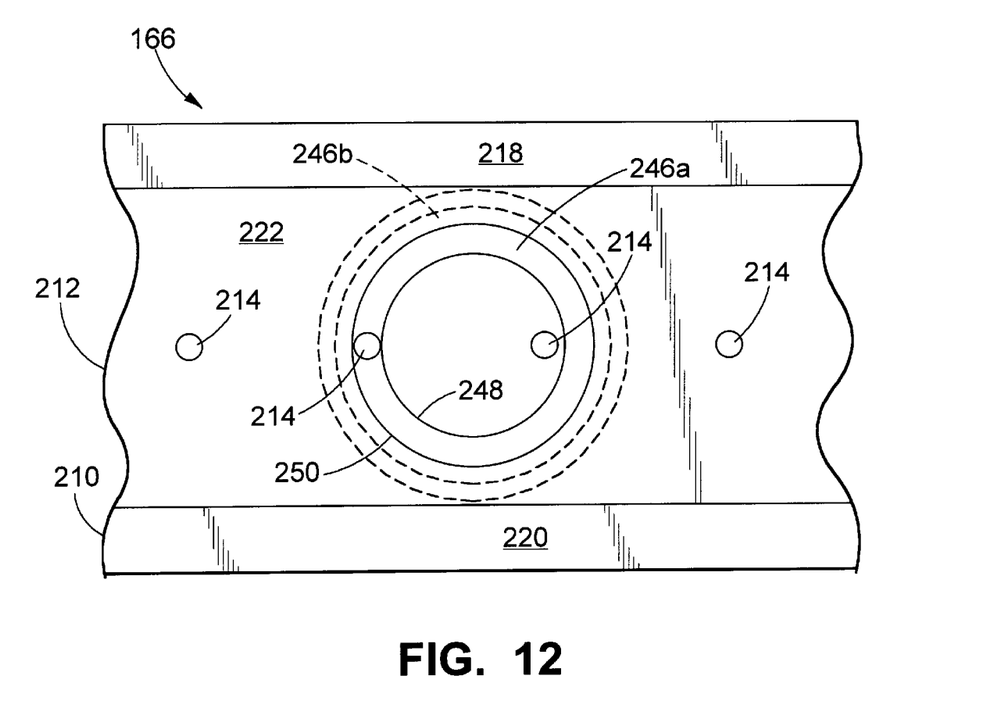
FIG. 12 is a bottom plan view of a portion of a preferred embodiment of a conveyor belt of this invention.

The conveyor belt 166 is specifically illustrated in FIGS. 9 and 12 and comprises an endless inner layer 210 and an endless outer layer 212 laminated to the endless inner layer 210 by suitable means such as an adhesive. A plurality of spaced apart fluid passageways 214 extend through the endless inner and outer layers 210 and 212. As illustrated in FIG. 12, the fluid passageways 214 preferably are circular in transverse cross section but it is understood that the fluid passageways can be of other geometrical cross-sectional configurations. A one way valve 216 is placed in each of the fluid passageways 214 and is wedge fitted into sealing engagement with portions of the sidewalls of the endless inner and outer layers 210 and 212. The one way valve 216 permits flow of air from the bottle 101, illustrated in FIG. 9, but prevents the flow of air into the bottle 101. As illustrated in FIG. 12, the endless inner layer 210 has a width in the cross machine direction that is greater than the width of the endless outer layer 212 in the cross machine direction so that the endless inner layer 210 has opposite side edge portions 218 and 220 projecting outwardly from a central body portion 222 defined by the endless outer layer 212.

Although a bottle 101 is illustrated in the drawings, it is understood that the vacuum conveyor illustrated in FIGS. 7–12 may be used to transport any hollow object that will form a cavity when a continuous portion thereof will be moved against the conveyor belt 166 so that a vacuum can be formed in such cavity. Also, the continuous portion can be of any desired cross-sectional configuration.

Figure 10:
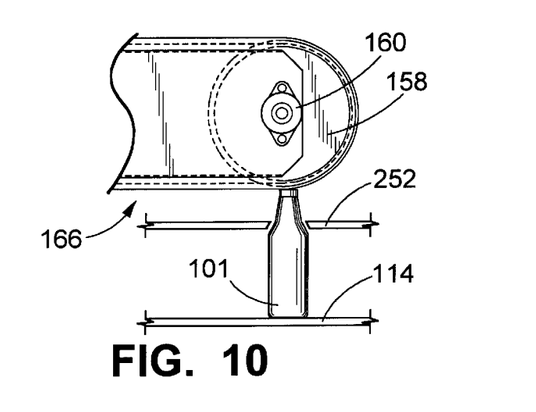
FIG. 10 is a schematic illustration of a portion of a preferred embodiment of the invention.

A second guide apparatus 230, illustrated in FIGS. 9 and 10, is provided for guiding the movement of the conveyor belt 166 over the lower surface 174. Although the second guide apparatus 230 can be mounted directly on the lower surface 174, a preferred embodiment of the invention, illustrated in FIG. 9, has a plate 232 secured to the lower surface 174 by any suitable apparatus such as an adhesive. The plate 232 is preferably formed from a plastic material having a relatively low coefficient of friction. The plate 232 has an aperture 234 that has a cross-sectional configuration similar to the slot 200 and is aligned therewith. As illustrated in FIG. 9, the slots 200 and 234 have a width greater than the width of the fluid passageway 214 to ensure that each fluid passageway 214 is exposed to the vacuum source. Also, this ensures that the portion of the endless inner layer 210 surrounding the fluid passageway is in contact with the adjacent portion of the plate 232. The second guide apparatus 230 comprises two spaced apart L-shaped members 236 and 238 that are secured to the plate 232 by suitable apparatus such as by threaded bolts and nuts passing through the openings 240, FIG. 11. Each of the L-shaped members 236 and 238 has chamfered entrance portions 242 and chamfered exit portions 244. As illustrated in FIG. 9, portions of the opposite edge portions 218 and 220 of the endless inner layer 210 are located between portions of the L-shaped members 236 and 238 and portions of the plate 232. Although the size of the neck 246 of the bottle 101 in FIGS. 8 and 9 is almost as wide as the width of the endless outer layer 212, it is understood that bottles 101 having smaller necks 246 can be carried by the conveyor belt 166.

In FIG. 12, there is illustrated how the sizes of necks 246*a* and 246*b* of differing bottle sizes may be carried by the endless outer layer 212. As illustrated in FIG. 12, neck 246*b* is larger than neck 246*a*. It is understood that all sizes of necks 246 inbetween 246*a* and 246*b* can be carried by the endless outer layer 212. The fluid passageways 214 are preferably spaced apart a distance to ensure that the smaller neck 246*a* will be exposed to at least one complete fluid passageway 214. This is accomplished by spacing the centers of two successive passageways 214 a distance apart substantially equal to the diameter of the inner portion 248. Also, the outer periphery of the fluid passageway 214 has a thickness equal to the radial distance between the inner portion 248 and the outer portion 250 of the neck 246*a*. As illustrated in FIG. 12, two fluid passageways 214 are enclosed within the larger neck 246*b*. Only one of these fluid passageways 214 is used to create the vacuum force in the bottle of neck 246*b*. It is recognized that some of the fluid passageways 214 will not be used to support a bottle 101 during the movement of the conveyor belt 166 and that atmospheric air will be pulled through these fluid passageways 214 as they move over the apertures 234 and 200. It is understood that the structure in FIG. 12 is for illustration purposes only and that the width of the conveyor belt 166 may be as great as desired for a given purpose and that the sizes and locations of the other portions of the apparatus may be varied accordingly.

As the bottles 101 on the endless outer layer 212 approach the roll 158, it is necessary to apply a sufficient force on the bottles 101 to separate the bottles 101 from the endless outer layer 212. This is accomplished by a stationary abutment apparatus 252 having portions located to contact opposite projecting portions of the bottle 101. As illustrated in FIG. 10, as the bottle 101 tends to be lifted upwardly by the conveyor belt 166 as it moves around the roll 158, the opposite projecting portions of the stationary abutment apparatus 252 contact such outwardly projecting portions and guide the bottle 101 onto the conveyor 114 for movement therewith.

In a preferred embodiment of the invention, the distance between the centers of the rolls 158 and 162 is between about 3.0 and 4.0 feet and preferably about 3.0 feet. This distance may be varied by the tension adjusting apparatus 164 in the amount between plus or minus 2.0 inches. The endless inner layer 210 has a width of between about 1.0 and 2.0 inches and preferably greater than the width of the endless outer layer 212 and a thickness of between about 0.25 and 0.50 inch and preferably about 0.25 inch. The endless inner layer 210 is preferably formed from a material having a relatively low coefficient of friction, such as TEFLON; and has a Shore A durometer of at least 100. The endless outer layer 212 has a width of between about 1.0 and 2.0 inches and preferably about 1.25 inches and a thickness of between about 0.125 and 0.25 inch and preferably about 0.125 inch. The endless outer belt 212 is preferably formed from a plastic material that can be deformed but will readily resile and has a Shore A durometer of between about 30 and 50 and preferably about 40. Each fluid passageway 214 is cylindrical having a diameter of between about 0.125 and 0.375 and preferably of about 0.125 inch. Each one way valve 216 may comprise the type marketed by Flow Technologies under the trade designation membrane valve and has a shape corresponding to the fluid passageway 214 with an outer periphery slightly greater than the inner periphery of the fluid passageway 214 so that the one way valve 216 may be secured in the fluid passageway by frictional forces. The one way valve 216 has a length slightly less than the combined thicknesses of the endless inner and outer layers 210 and 212. The slots 200 and 234 have a width greater than the width of each of the fluid passageways 214 and a length of between about 0.25 and 0.50 inch and preferably about 0.312. The vacuum chamber 190 is connected to a vacuum creating source so that the vacuum in the vacuum chamber 190 is between about 8.0 and 16.0 inches of mercury and preferably about 12.0 inches of mercury.

In operation a plurality of bottles 101 are guided for movement onto and with the conveyor 110 in a spaced apart relationship by conventional apparatus (not shown). The distance between the conveyor 110 and the lower reach 172 of the conveyor belt 166 is slightly less than the length of the bottle 101 so that the neck 246 of the bottle 101 will slightly deform the endless outer layer 212 as contact between them is made. The bottle 101, still supported by the conveyor 110 then passes under the slot 234 so that a vacuum is created in the bottle 101 through the fluid passageway 214 and the one way valve 216 so that the bottle is now supported by the conveyor belt 166 as the conveyor belt 110 ends. The one way valve 216 functions to retain the vacuum force on the bottle 101 so that it moves with the conveyor belt 166. The bottle 101 then passes through the bottle testing apparatus as described below. After passing through the bottle testing apparatus, each non-broken bottle moves with the conveyor belt 166 to a location over the conveyor 114. As the bottle 101 starts to move upwardly with the conveyor belt 166 adjacent to the roll 158, the bottle 101 contacts the stationary abutment 252 to have sufficient force applied thereto to separate the bottle 101 from the conveyor belt 166 and be positioned on the conveyor 114 for movement therewith.

The selection of acoustic frequency at which to drive the transducers 72, 74 will now be discussed. Applicant has discovered that a bottle having a fracture may be ruptured with a relatively low amount of energy compared to that required to rupture an unflawed bottle if the frequency of the sound wave applied to the bottle contains at least one and preferably multiple frequency components which are based upon physical dimensions of the bottle which correspond to natural frequencies of the bottle. For a bottle 10 of the type illustrated, the most important bottle dimensions are the bottle body length L, the bottle body diameter D, and the bottle body wall thickness T. Frequency components which are chosen for the tester sound wave are fundamental natural frequencies of the bottle and overtones of these fundamental natural frequencies. (A fundamental natural frequency of a bottle and all overtones of that fundamental frequency are referred to as a "natural frequency harmonic series". Any group of two or more frequencies of a natural frequency harmonic series is referred to herein as a "natural frequencies set." Any of the frequencies in a natural frequency harmonic series may be referred to herein simply as a "natural frequency".) It has been discovered that in bottles of the type illustrated in FIG. 1 that three important natural frequency harmonic series of the bottle are substantially inversely proportionate to bottle body length "L", bottle body diameter "D" and bottle body wall thickness "T", respectively. A bottle natural frequency harmonic series based upon the body length is about $c/2L$, $2c/2L$, $3c/2L$ . . . $nc/2L$ where c is the speed of sound in glass. The value $c/2L$ is the fundamental frequency or first harmonic frequency; $2c/2L$ is the first overtone or second harmonic; $2c/3L$ is the second overtone or third harmonic, etc. A natural frequency harmonic series associated with bottle body diameter is $c/2d$, $2c/2d$, $3c/2d$, - - - $nc/2d$. The natural frequency harmonic series associated with bottle thickness is $c/2t$, $2c/2t$, $3c/2t$, $nc/2t$. Depending upon the configuration of the bottle, other natural frequencies may become important and/or may replace the above frequencies in the mixed frequency sound wave generated by the transponders. Accordingly, the invention is not to be considered limited to any particular bottle parameter or set of frequencies since bottle parameters and associated natural frequencies to be employed will vary depending upon bottle configuration. For the described "convenience" bottle, a combination of three natural frequency sets based upon all three described bottle parameters "L," "D" and "T" is desirable. In order to vibrate a bottle at a natural frequency, it is necessary to produce a sound wave having a frequency component which includes at least one frequency of that natural frequency harmonic series. However, it is preferable to use a natural frequency set, i.e. multiple frequencies from that harmonic series which most preferably include at least the first two harmonics. Each added harmonic increases the energy which may be applied.

Since the dimensions of a bottle may vary slightly from one batch to another and from mold to mold during manufacturing, in order to test a series of bottles having the same general configuration, it is necessary to take into account the bottle tolerance in each of the dimensions which are used as the basis for determining the natural frequency components of the sound waves applied to the bottles. In order to take into consideration this variation in dimensions from bottle to bottle, applicant has discovered that it is useful to vary the frequency of each frequency component associated with a particular bottle by an amount at least equal to the expected deviation between bottles. This is accomplished by oscillating or sweeping the particular frequency components associated with a bottle parameter over a frequency range associated with the tolerance of that bottle parameter. For example, if the tolerance of bottle body length were plus or minus 5%, then a fundamental natural frequency component associated with body length would be oscillated through the range of frequencies $c/2$ (1+/−5%) and the harmonics thereof would be similarly oscillated. An exemplary oscillation cycle length for each frequency component is 0.02 seconds.

In one exemplary embodiment the natural frequency set associate with dimension "L" employs the first two harmonics which are each swept. The swept frequency range associate with the first harmonic is 2800 Hz to 3150 Hz and the swept frequency range associated with the second harmonic is 5216 Hz to 5841 Hz.

It will be appreciated from the above description that the frequency mix selected for the acoustic bottle tester 60 is designed to vibrate the bottle at one or more of its natural frequencies. The relatively large magnitude standing waves produced in the bottle as a result of vibrating at one or more natural frequencies will tend to cause any bottle to rupture. However, a bottle which has been weakened by a fracture will rupture at a much lower energy level than a pristine bottle. If the bottle is exposed to sound waves which do not include a frequency component which is one of the natural frequencies of the bottle, then even a fractured bottle is unlikely to rupture unless it is exposed to an enormous amplitude sound wave. Thus, the success of using a bottle tester of this type is to a large extent determined by proper selection of bottle natural frequency sets. These natural frequency sets may be selected through empirical means as by applying a relatively large amplitude sound wave to the bottle and varying the frequency until fracture occurs or may be approximated through measurement of the above-described bottle parameters in a bottle of the type illustrated in FIG. 1, and then fine tuning those values empirically. Once the desired natural frequency set(s) for a bottle configuration is determined, the power level setting needed to rupture a bottle of a selected flaw type, e.g., a moderately abraded bottle (as provided by roughing with 320 grit sandpaper) is determined by empirical testing on bottles having this type of flaw. For example, a bottle having this type of flaw could be placed in alignment with the acoustic drivers and a sound wave applied thereto—initially at a low power level which is gradually increased until the bottle breaks. The power level which broke the first bottle would then be used to test other bottles with the same flaw and would be adjusted upwardly slightly, if necessary, to ensure that it was of sufficient magnitude to break all bottles having this flaw type. The tester could then be used for online testing and would rupture all bottles having flaws of the selected magnitude or worse.

It is contemplated that the inventive concepts herein described may be variously otherwise embodied and it is intended that the appended claims be construed to include alternative embodiments of the invention, except as limited by the prior art.

What is claimed is:

1. A vacuum conveyor comprising:
    a housing having a first end portion, a central portion and a second end portion;
    said housing connected to a vacuum forming source to form a vacuum in at least said first end portion of said housing;
    a conveyor belt mounted for movement around portions of said housing;
    said conveyor belt having a plurality of spaced apart fluid passageways formed therein;
    only said first end portion of said housing having at least one aperture formed therein;
    said conveyor belt being mounted so that said plurality of spaced apart fluid passageways pass over said at least one aperture so that a hollow object having an opening formed therein and in contact with said conveyor belt and surrounding at least one of said plurality of spaced apart fluid passageways will have a vacuum formed therein and be held in contact with said conveyor belt by a vacuum force; and
    apparatus for maintaining said vacuum force on said hollow object after said hollow object has moved past said at least one aperture until a sufficient force is applied to said hollow object to separate said hollow object from said conveyor belt.

2. A vacuum conveyor as in claim 1 wherein:
    said at least one aperture having a length extending in a direction parallel to the direction of movement of said conveyor belt and a width extending in a direction transverse to the direction of movement of said conveyor belt;
    said plurality of spaced apart fluid passageways are equally spaced apart;
    said length being greater than said width; and
    said length having an extent less than the distance between adjacent ones of said plurality of equally spaced apart fluid passageways.

3. A vacuum conveyor as in claim 2 wherein:
    successive ones of said plurality of equally spaced apart fluid passageways are spaced apart a distance so that the total cross-sectional area of at least one of said equally spaced apart fluid passageways is within the inner diameter of said opening of said hollow object.

4. A vacuum conveyor as in claim 1 wherein said apparatus comprises:
    a one way valve for permitting air to be drawn out of said hollow object but preventing air from entering into said hollow object associated with each one of said plurality of spaced apart fluid passageways.

5. A vacuum conveyor as in claim 4 wherein:
    said at least one aperture is the only aperture formed in said first end portion.

6. A vacuum conveyor as in claim 4 wherein:
    said at least one aperture having a length extending in a direction parallel to the direction of movement of said conveyor belt and a width extending in a direction transverse to the direction of movement of said conveyor belt;
    said plurality of spaced apart fluid passageways are equally spaced apart;
    said length being greater than said width; and
    said length having an extent less than the distance between adjacent ones of said plurality of equally spaced apart fluid passageways.

7. A vacuum conveyor as in claim 6 and further comprising:
    successive ones of said plurality of equally spaced apart fluid passageways are spaced apart a distance so that the total cross- sectional area of at least one of said equally spaced apart fluid passageways is within the inner diameter of said opening of said hollow object.

8. A vacuum conveyor in claim 1 wherein:
    said housing having a length that is greater than its width;
    a vacuum chamber located in said first end portion;
    said vacuum chamber being connected to said vacuum forming source; and
    said at least one aperture being formed in said vacuum chamber.

9. A vacuum conveyor as in claim 8 and further comprising:
    a first roll mounted for rotation at the beginning of said first end portion;
    a second roll mounted for rotation at the ending of said second end portion;
    said conveyor belt moving around said first and second rolls;
    said housing having an upper surface and a lower surface;
    a first guide apparatus for guiding the movement of said conveyor belt over said upper surface; and
    a second guide apparatus for guiding the movement of said conveyor belt over said lower surface.

10. A vacuum conveyor as in claim 9 and further comprising:
    said second guide apparatus applying a force on said conveyor belt to hold a portion of said conveyor belt in contact with said lower surface surrounding said at least one aperture so that said opening of said hollow object, which is in contact with said conveyor belt, is subjected to said vacuum force as it passes under said at least one aperture.

11. A vacuum conveyor as in claim 10 wherein:
    said conveyor belt having opposite side edge portions and a central body portion; and
    said opposite side edge portions being located between said lower surface and said second guide apparatus.

12. A vacuum conveyor as in claim 11 wherein:
    said hollow object comprises a bottle; and
    said bottle having a neck portion having an opening formed therein so that the portion of said neck portion surrounding said opening contacts said central body portion.

13. A vacuum conveyor as in claim 12 and further comprising:
   bottle testing apparatus located adjacent to said central portion so that said bottle is exposed to said bottle testing apparatus; and
   said bottle testing apparatus breaking flawed bottles so that the vacuum holding force is removed and all of the broken bottle falls away from said conveyor belt.

14. A vacuum conveyor as in claim 8 wherein said apparatus comprises:
   a one way valve for permitting air to be drawn out of said hollow object but preventing air from entering into said hollow object associated with each one of said plurality of spaced apart fluid passageways.

15. A vacuum conveyor as in claim 14 wherein:
   said at least one aperture is the only aperture formed in said first end portion.

16. A vacuum conveyor as in claim 15 wherein:
   said at least one aperture having a length extending in a direction parallel to the direction of movement of said conveyor belt and a width extending in a direction transverse to the direction of movement of said conveyor belt;
   said plurality of spaced apart fluid passageways being equally spaced apart;
   said length being greater than said width; and
   said length having an extent less than the distance between adjacent ones of said plurality of equally spaced apart fluid passageways.

17. A vacuum conveyor as in claim 16 and further comprising:
   successive ones of said plurality of equally spaced apart fluid passageways are spaced apart a distance so that the total cross-sectional area of at least one of said equally spaced apart fluid passageways is within the inner diameter of said opening of said hollow object.

18. A vacuum conveyor as in claim 8 wherein said conveyor belt comprises:
   and endless inner layer;
   an endless outer layer laminated to said endless inner layer;
   said endless inner layer having a width greater than the width of said endless outer layer transverse to the direction of movement of said conveyor belt so that said conveyor belt has opposite side edge portions and a central body portion; and
   each of said plurality of spaced apart fluid passageways extending through said endless inner and outer layers.

19. A vacuum conveyor as in claim 18 and further comprising:
   a first roll mounted for rotation at the beginning of said first end portion;
   a second roll mounted for rotation at the ending of said second end portion;
   said conveyor belt moving around said first and second rolls;
   said housing having an upper surface and a lower surface;
   a first guide apparatus for guiding the movement of said conveyor belt over said upper surface;
   a second guide apparatus for guiding the movement of said conveyor belt over said lower surface;
   said second guide apparatus applying a force on said conveyor belt to hold a portion of said conveyor belt in contact with said lower surface surrounding said at least one aperture so that said opening of said hollow object, which is in contact with said conveyor belt, is subjected to said vacuum force as it passes under said at least one aperture; and
   said opposite side edge portions being located between said lower surface and said second guide apparatus.

20. A conveyor for exposing bottles to a bottle testing apparatus for testing bottles for flaws of a predetermined magnitude and wherein said bottle testing apparatus breaks any bottle having a flaw of the predetermined magnitude comprising:
   a housing having a length that is greater than its width;
   said housing connected to a vacuum forming source to form a vacuum in said housing;
   a conveyor belt having an upper reach and a lower reach and journalled for movement around said housing in a lengthwise direction;
   said conveyor belt having a plurality of spaced apart fluid passageways formed therein;
   said lower reach being exposed to said vacuum in said housing so that a plurality of bottles in a spaced apart relationship move with said lower reach; and
   a bottle testing apparatus located so that each one of said plurality of bottles moving with said lower reach is exposed to said bottle testing apparatus so that when a flawed bottle beaks all the fragments thereof will fall into a fragment collection system.

* * * * *